(12) United States Patent
Baserga et al.

(10) Patent No.: US 6,218,363 B1
(45) Date of Patent: Apr. 17, 2001

(54) MHC PEPTIDES AND METHODS OF USE

(75) Inventors: Renato L. Baserga, Ardmore; Mariana Resnicoff; Ziwei Huang, both of Philadelphia, all of PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 08/704,344

(22) Filed: Aug. 28, 1996

(51) Int. Cl.$^7$ ...................................................... A61K 38/00
(52) U.S. Cl. .............................. 514/15; 530/328; 530/395
(58) Field of Search .............................. 514/15; 530/328, 530/395

(56) References Cited

U.S. PATENT DOCUMENTS 5,679,641 * 10/1997 Melief et al. ........................... 514/15

FOREIGN PATENT DOCUMENTS

| 9321948 | * | 11/1993 | (WO) . |
| 9324525 | * | 12/1993 | (WO) . |
| 9522561 | * | 8/1995 | (WO) . |
| 9529193 | * | 11/1995 | (WO) . |
| 9528958 |   | 11/1995 | (WO) . |

OTHER PUBLICATIONS

Dayhoff, *Atlas of Protein Sequence and Structure*, vol. 5, p. 96, 1972.*

HCAPLUS AN 1995: 998364, WO 9528958, Nikolic–Zugic et al. (abstract), 1995*

* cited by examiner

*Primary Examiner*—Dwayne C. Jones
*Assistant Examiner*—C. Delacroix-Muirheid
(74) *Attorney, Agent, or Firm*—Hale and Dorr LLP

(57) ABSTRACT

MHC or HLA Class I peptides and compositions thereof are provided for the specific induction of apoptosis of cancer cells in a patient. Methods of treating cancer cells in patients suffering from cancer employing the MHC or HLA Class I peptides of the invention. Also provided are methods of identifying MHC or HLA Class I peptides and variants thereof capable of killing cancerous cells in vivo in a patient suffering from cancer.

12 Claims, 2 Drawing Sheets

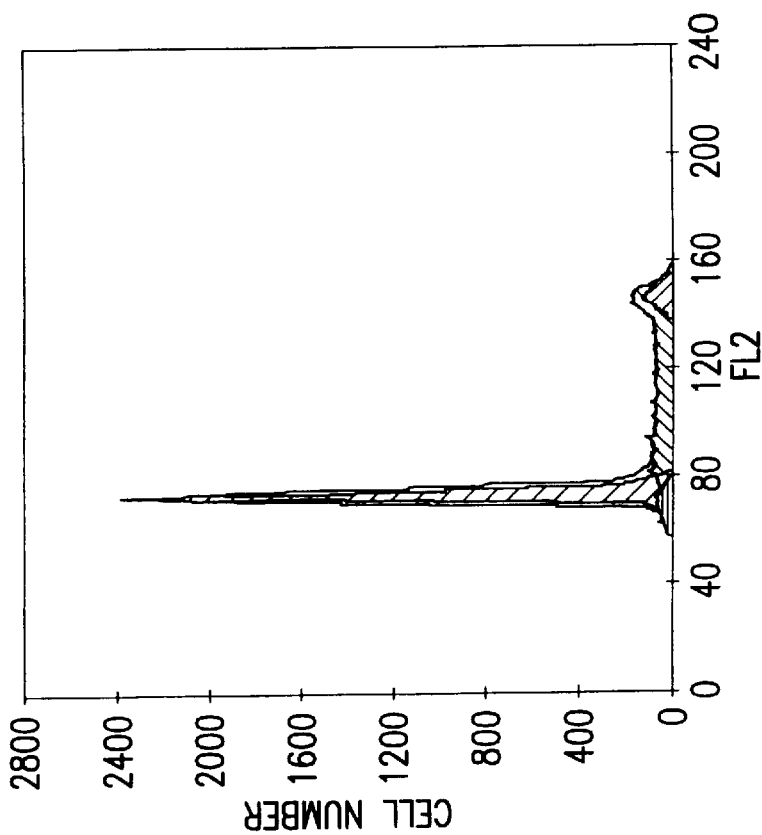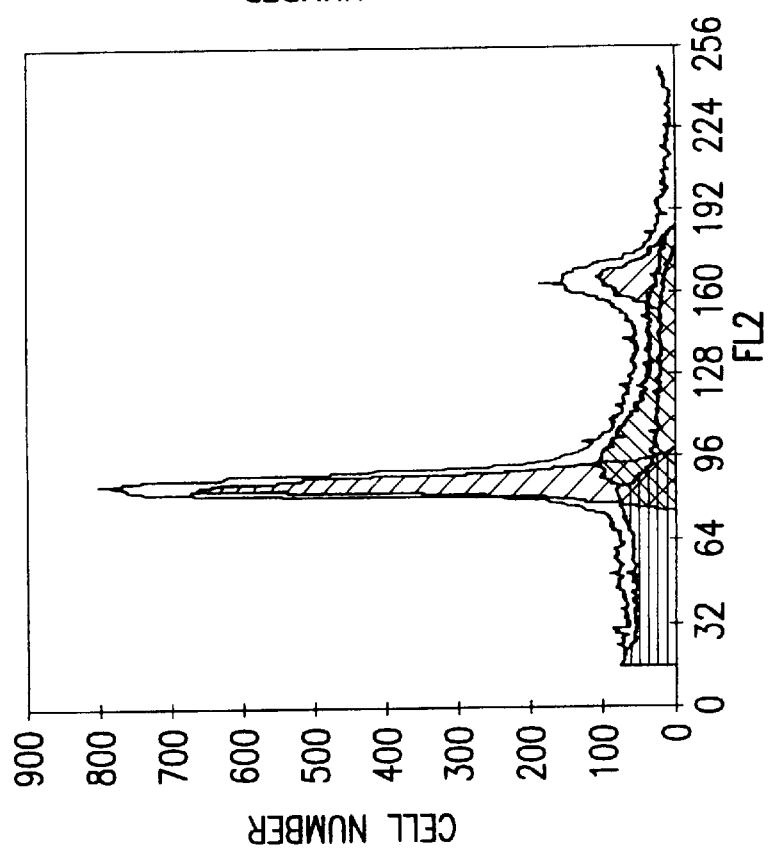

MHC PEPTIDES AND METHODS OF USE

FIELD OF THE INVENTION

The present invention relates generally to the field of cell physiology, and more particularly, to programmed cell death, or apoptosis. The novel peptides, compositions and methods of the invention are useful for modulating cell cycle events in cells, particularly in cancer cells.

BACKGROUND OF THE INVENTION

It is estimated that nearly one-third of all individuals in the United States will develop cancer. While early diagnosis and treatment of this disease has increased the five year relative survival rate to nearly 50%, cancer remains second only to cardiac disease as the leading cause of death; approximately 20% of Americans die from cancer each year.

Cancer cells (also referred to as neoplastic or malignant cells) can be defined in terms of four characteristics as to which they differ from normal cells. "Clonality" refers to the fact that most cancer originates from a single stem cell which proliferates to form a clone of malignant cells. "Autonomy" refers to the fact that the growth of malignant cells is not properly regulated by normal biochemical and physical influences in the environment. "Anaplasia" refers to the lack of normal, coordinated cell differentiation which characterizes malignant cells. "Metastasis" is the characteristic capacity of cancer cells for discontinuous growth and dissemination to other parts of the body.

While each of these characteristics can be expressed by normal, non-malignant cells at certain appropriate times during development, cancer cells exhibit these characteristics in an inappropriate or excessive manner. Many approaches to the diagnosis and treatment of cancer have sought to take advantage of these characteristic differences. In particular, many forms of cancer demonstrate unusual sensitivity to radiation and chemotherapy. In addition to, or in combination with, traditional surgical excision, gains in treatment of cancers, including acute leukemia, lymphoproliferative malignancies, testicular and breast cancer, have been realized.

Limitations of these forms of treatment, including undesirable side effects, have lead medical investigators to seek new treatment modalities, including immunotherapy. Malignant cells are sufficiently different from normal cells to be recognized and destroyed by the immune system.

One approach to immunotherapy against tumors exploits cytolytic T lymphocytes (CTL), which are key immune cells in the body believed to direct the attack on cancer cells. The basis of this approach is that the identification of tumor cell-specific antigens not found on normal cells should lead to the generation of CTL capable of attacking and lysing the cells which make up a cancerous tumor. (See, e.g., Boone, T., et al., *Ann. Rev. Immunol.* 12:337–65 (1994); Van Pel, A., et al., *Immunol. Rev.* 145:229–250 (1995); Boone, T., et al., *Immunol. Today* 16:334–36 (1995)).

Investigators have also recognized, however, that in many instances, known tumor cell specific antigens are insufficiently immunogenic to bring about CTL activation. Accordingly, some have looked to generate a cellular immune response in patients (i.e., to achieve vaccination against cancer) by presenting the patient's immune system with the putative antigen, together with an adjuvant, such as the B7 protein and various cytokines including interleukin-2 and interferon γ, granulocyte-macrophage colony-stimulating factor (GM-CSF) and interleukin-4. (See, e.g., Rosenberg, A., *J. Clin. Oncol.* 10:180–199 (1992); Marchand, M., et al., *Dermatol.* 186:278–280 (1993); Marchand, M., et al., *Rnt. J. Cancer* 63:883–85 (1995)). A number of tumor cell-specific antigens, including MAGE-1, MAGE-3, and MART for melanoma and E6 and E7 for human papillomavirus (HPV)-associated cervical carcinoma, are in preliminary human clinical trials.

It is also known that CTL recognize tumor cell-specific antigens which are presented by Major Histocompatibility Complex (MHC) Class I glycoproteins. These glycoproteins, along with MHC Class II glycoproteins, immunoglobulins and T cell receptors (TCRs), make up families of antigen binding molecules responsible for specificity, repertoire and memory in the immune response. Although the somatic rearrangement of their immunoglobulin or TCR genes restricts individual B and T cells to a single specificity for antigen, millions of specificities are possessed by the immune system as a population of cells. Immunoglobulin receptors on B cells bind to native protein antigens, whereas TCRs recognize short peptide fragments bound by polymorphic MHC glycoproteins. Diverse species, ranging from cattle to chickens to amphibians to humans, have an MHC region. The human MHC, known as the Human Leukocyte Antigen (HLA) region, is located on the short arm of chromosome 6. Because of its importance in self/non-self discrimination for tissue transplantation in humans, the bulk of knowledge about the MHC region has come from studies on human and murine MHCs.

The size and other physical characteristics of MHC Class I peptides and the structural basis for their direct binding to MHC Class I glycoproteins has been elucidated based on crystallographic studies of the HLA-A2 molecule. (See, e.g., Engelhard, V. H., *Ann. Rev. Immunol.* 12:181–207 (1994)), and investigators have attempted to achieve vaccination against cancer cells by injecting such peptides (Id.; Marchand, M., et al., *Int. J. Cancer* 63:883–85 (1995)). However, this approach is also subject to the limitations described above for other vaccination methods.

Accordingly, there exists a need for methods and compositions for the therapeutic treatment of cancer in patients suffering therefrom which would overcome or obviate the limitations of available approaches.

BRIEF DESCRIPTION OF THE DRAWINGS

FIG. 1. Fluorescence Activated Cell Sorting Analysis of C6 Cells Treated In Vivo with MHC Class I Peptide Demonstrates Specificity of Toxic Effect.

FIG. 1(A). C6 cells treated with active peptide YLEPG-PVTA [SEQ ID NO:2].

FIG. 1(B). C6 cells treated with control peptide SMAPGNYSV [SEQ ID NO:14].
C6 cells in both Figures were incubated in vivo for 90 minutes in a diffusion chamber as described herein.

Figure 2:
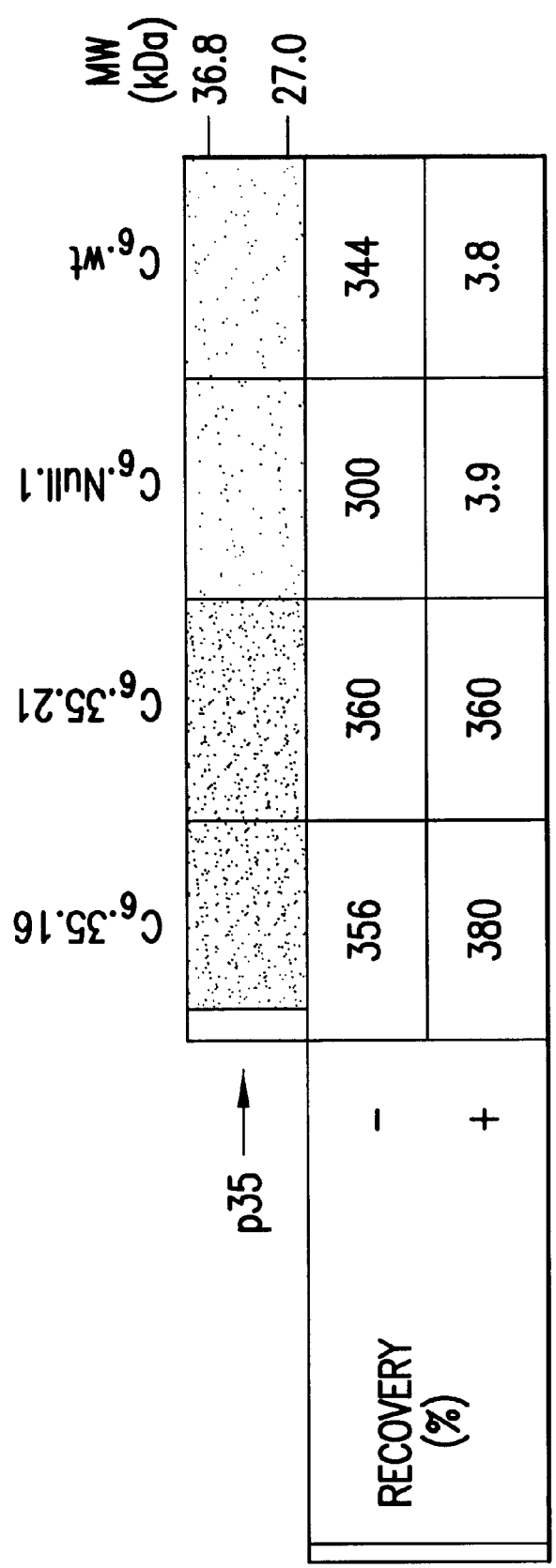
FIG. 2. Expression of Baculovirus p35 Protein that Inhibits Apoptosis by Inhibiting ICE-like Proteases, Prevents MHC Class I Peptide-Induced Apoptosis in C6 Cells In Vivo.

Expression of p35 is shown in various cell lines. The percentage of cells recovered from the diffusion chamber is shown for cells treated with the synthetic peptide YLRPG-PVTA (SEQ. ID NO: 4) (+) and control cells that were not exposed to the peptide (−). Only C6 cells and C6 cells stably transfected with the empty vector underwent apoptosis when treated with the peptide. Clones expressing the p35 protein grew in the diffusion chamber equally well, whether untreated or incubated with the synthetic peptide.

SUMMARY OF THE INVENTION

It has now been unexpectedly found that MHC Class I peptides and compositions comprising these peptides exhibit in vivo and in vitro specific toxicity against tumor cells. Although not intending to be bound by any particular theory, it is believed that this specific toxicity occurs via the induction of apoptosis in those cells. Surprisingly, the toxic effect of MHC Class I peptides and compositions comprising them is independent of the immune system. Accordingly, the peptides, compositions and therapeutic methods of the present invention are not subject to the limitations of immunotherapeutic approaches to cancer treatment.

It has further surprisingly been found that the peptides and peptide compositions of the present invention exhibit specific toxicity in vivo in a variety of tumor cells, and are not limited to a specific tumor type or mammalian species.

An advantage of the present invention is that the therapeutic MHC Class I peptides and compositions will be effective for resectable and non-resectable (i.e., metastasizing) cancers, as well as for cancers which do not lend themselves easily to treatment by traditional radiation and chemotherapeutic methods, such as cancers of the lung. Further, because cancer cells are more sensitive than normal cells to the toxic effects of the peptides of the invention, the methods of the present invention allow for aggressive treatment of cancers in patients without the undesirable side effects often associated with conventional radiation and chemotherapy treatment.

Accordingly, it is an object of the present invention to provide MHC Class I peptides and compositions thereof capable of exhibiting specific toxicity against cancer cells in a patient.

It is another object of the present invention to provide for methods of treating cancer cells in patients suffering from cancer.

A further object of the present invention is to provide methods of identifying MHC Class I peptides and variants thereof capable of exhibiting specific toxicity against cancerous cells in vivo in a patient suffering from cancer. Yet a further object of the present invention is to provide a method for the treatment of cancer which is independent of an immune mechanism.

Another object of the present invention is to provide MHC Class I peptides, compositions thereof and methods for the induction of apoptosis in vivo on a variety of tumor cell types and in different mammalian species, including humans.

These and other objects of the present invention will be apparent to those of skill from the description which follows, including illustrative non-limiting embodiments of the compositions and methods of the present invention.

DETAILED DESCRIPTION OF THE INVENTION

Technical and scientific terms used herein have the meanings commonly understood by one of ordinary skill in the art to which the present invention pertains, unless otherwise defined. Reference is made herein to various methodologies known to those of skill in the art. Publications and other materials setting forth such known methodologies to which reference is made are incorporated herein by reference in their entireties as though set forth in full. Standard reference works setting forth the general principles of recombinant DNA technology include Sambrook, J., et al., *Molecular Cloning: A Laboratory Manual*, 2d Ed., Cold Spring Harbor Laboratory Press, Plainview, N.Y. (1989); Kaufman, P. B., et al., Eds., *Handbook of Molecular and Cellular Methods in Biology and Medicine*, CRC Press, Boca Raton (1995); McPherson, M. J., Ed., *Directed Mutagenesis: A Practical Approach*, IRL Press, Oxford (1991); Jones, J., *Amino Acid and Peptide Synthesis*, Oxford Science Publications, Oxford (1992); Austen, B. M. and Westwood, O. M. R., *Protein Targeting and Secretion*, IRL Press, Oxford (1991). Any suitable materials and/or methods known to those of skill can be utilized in carrying out the present invention; however, preferred materials and/or methods are described. Materials, reagents and the like to which reference is made in the following description and examples are obtainable from commercial sources, unless otherwise noted.

The present invention is directed broadly to methods for the therapeutic treatment of cancer cells in vivo comprising administering to a patient suffering from cancer an effective amount of a composition comprising one or more MHC Class I peptides to interfere with the growth and/or proliferation of all or a portion of the target cancer cells in the patient. MHC Class I peptides useful according to the methods of the invention are preferably selected for use according to the invention by means of an in vitro or in vivo apoptosis assay. Presently preferred is the in vivo apoptosis assay based upon the diffusion chamber methods described in detail by Resnicoff, M., et al., *Cancer Res.* 55:2463–2469 (1995). The cells used for the screening assay are most preferably target cancer cells obtained from the patient by conventional means including, but not limited to, tissue biopsy. In particular, where a cancerous tumor has been substantially excised from a patient and it is desired to insure that any cancer cells which may remain in the patient following surgery are treated, cells from the excised tumor may be employed in the screening assay to identify one or more MHC Class I peptides for post-surgery treatment of the patient.

Peptides useful in the methods of the invention are preferably MHC Class I peptides, or variants or mutants thereof, capable of exhibiting specific toxicity in vivo against the target cancer cells of a patient, and may be selected, as described herein, by means of in vitro or in viva apoptosis assays. Peptides so selected may be isolated and purified from natural sources. Such sources may include the target cancer cells themselves as described above. However, it has surprisingly been found that useful peptides according to the invention are capable of exhibiting specific toxicity in vivo against a variety of tumor cell lines, regardless of tumor type or species.

Accordingly, where a sample of cells from a patient's tumor or other cancerous tissue is not available, other peptides may be selected for administration on the basis of their ability to kill cells as demonstrated by an appropriate screening assay. In making such a selection, it may be desirable to select peptides which have demonstrated an ability to kill cancer cells or cell from cell lines related to the cancer from which the patient suffers. Nonlimiting examples of presently preferred cell lines for this purpose are set forth in Table 10. Selected peptides may include peptides which have demonstrated specific toxicity (which may or may not occur via the induction of apoptosis) against the cells of other patients suffering from the same or similar forms of cancer as the patient whom it is desired to treat. Presently preferred peptides include:

| | |
|---|---|
| LLDGTATLRL | SEQ ID NO: 1 |
| YLEPGPVTA | SEQ ID NO: 2 |
| FECNTAQPG | SEQ ID NO: 3 |
| YLRPGPVTA | SEQ ID NO: 4 |
| YLEXGXVTA (X: N-Methyl-A) | SEQ ID NO: 5 |
| YLEPGPVKA | SEQ ID NO: 6 |
| YLAPGPVTA | SEQ ID NO: 7 |
| YLEPGPVAA | SEQ ID NO: 8 |
| YLEPGPATA | SEQ ID NO: 9 |
| YLEPAPVTA | SEQ ID NO: 10 |
| YLRPGPVRA | SEQ ID NO: 11 | and functional equivalents thereof.

Sequence ID No: 1, a MHC Class I peptide derived from gp100, was described by Kawakami, et al., *Proc. Natl. Acad. Sci. USA* 91(14):6458–6462 (1994), as a human melanoma specific antigen. Sequence ID No: 2, reported by Cox, et al., *Science* 294:716–719 (1994), is recognized by melanoma-specific human CTL lines. Sequence ID No: 3, described by Mandelboim, et al., *Nature* 369:67–71 (1994), is derived from connexin 37, and induces CTL responses against murine lung carcinoma. These peptides reduce recovery of C6 cells by 95% or more in an in vivo apoptosis assay, as compared with control peptides.

Mutation of MHC Class I peptides is one method by which variants of these peptides may be produced which are suitable for use according to the invention. Such variants may conveniently be screened as described herein without undue experimentation, and will provide a means by which additional useful peptides may be produced. Presently preferred variants include the inverted D-amino acid forms of known MHC Class I peptides. Data presented herein show them to be surprisingly as effective as their respective L-amino acid peptide forms in inducing apoptosis, and they may be desirable for patient administration. Presently preferred D-amino acids include:

| | |
|---|---|
| ATVPGPELY | SEQ ID NO: 12 |
| LRLTATGDLL | SEQ ID NO: 13 |

SEQ ID NO: 12 is the inverted D-amino acid peptide of SEQ ID NO: 2 and SEQ ID NO: 13 is the inverted D-amino acid peptide of SEQ ID NO: 1.

Similarly, point mutations may be introduced into known MHC Class I peptides to produce variants thereof useful in the methods of the present invention. The variants so produced may be evaluated by means of a screening assay to determine whether the resulting peptide may be suitable for use according to the invention. The inventors found that certain mutations do not affect the ability of the peptide variants to exhibit specific toxicity, while others completely abrogate the effect. Illustrative examples of point mutations and their effect on cytotoxic capacity are shown in Table 1; however, the key criterion is that the resulting peptide variant be capable of exhibiting specific toxicity, which will be evident from a screening assay which may be routinely run by those of skill.

Other variations in the peptides of the invention may be desirable, for example, to increase or decrease the half life of the resulting peptide in the bloodstream or tissue. Thus, it is within the contemplated scope of the present invention to produce variants of peptides useful according to the methods of the invention, by introducing therein alterations, such as are known in the art, which may include the use of synthetic or non-traditional amino acid residues, side chains, non-amide bonds as in peptoides, and the like, which may act as blocking groups to protect the peptide against degradation. These and other methods of modifying peptides are well known in the art.

Peptides useful according to the invention may be isolated from natural sources and purified. However, it is preferred to synthesize the peptides, which will typically be of relatively short length, by means well known in the art. Preferred is solid phase synthesis with Fmoc-strategy, although any suitable method of synthesis may be employed.

Preferred peptides and peptide compositions useful according to the present invention include MHC Class I peptides and, more preferably, HLA Class I peptides, and their variants. Such peptides and variants thereof are generally defined by their capacity to bind to MHC or HLA Class I glycoprotein molecules. Peptides bound by HLA class I molecules are the products of cytoplasmic degradation of cellular proteins that are transported into the endoplasmic reticulum. There they associate with a polymorphic HLA-A, -B, or -C heavy chain and the invariant $\beta_2$-microglobulin ($\beta_2$-M) to form a stable trimer that moves to the cell surface (S. Kvist and F. Lévy, *Semin, Immunol.* 5:105 (1993). In healthy cells, the peptides are derived from normal cellular proteins, and the immune system is rendered tolerant to these peptides during development. Upon infection of cells, Class I molecules loaded with pathogen-derived peptides are generated and recognized by cytolytic $CD8^+T$ cells that then kill the infected cells (A. Townsend and H. Bodmer, *Annu. Rev. Immunol.* 7:601 (1989); R. M. Zinkernagel, *Science* 271:173 (1996).

The peptides bound by a particular Class I allotype are defined by positions within the peptide sequence that are restricted to one or a few amino acids. The preferred residues are termed anchors because their side chains extend into pockets of the binding site. In aggregate, HLA Class I allotypes have a range of Class I peptide binding motifs that covers the spectrum of peptide characteristics: acidic, basic, neutral, and hydrophobic. O. Rötzschke, K. Falk, O. Stevanovic, G. Jung, H. G., Rammensee, *Nature* 351:290 (1991); K. Falk and O. Rötzschke, *Semin. Immunol.* 5:81 (1993). (See, Parham, P., and Ohta, T., *Science* 272:67–74 (1996). Preferred peptides according to the present invention will include those which comprise amino acid residues having side chains which extend into the pockets of the binding site. Such peptides and variants thereof which are capable of achieving specific binding to MHC or HLA Class I glycoproteins are contemplated as falling within the scope of the invention. The suitability of a particular peptide or peptide variant for the exhibition of specific toxicity against a target cancer cell will be determined by those of skill by means, for example, of the in vivo apoptosis assay as described herein, or by other known methods, without the exercise of undue experimentation. Sequencing of peptides derived from cancer or other cells and which bind to MHC or HLA Class I glycoproteins may be accomplished by known methods. Examples of such methods are described, for example, in Hancock, W., ed., *New Methods in Peptide Mapping for the Characterization of Proteins*, CRC Press, Boca Raton, Fla. Publisher (1996).

An understanding of the structure of MHC Class I glycoproteins is of importance in selecting binding peptides and variants useful according to the invention. Generally, MHC Class I glycoproteins comprise a glycosylated polypeptide chain of 45 kDa (heavy chain) in close, non-covalent association with beta$_2$ microglobulin ($\beta_2$m), a 12 kDa polypeptide which is also found unassociated in serum. Amino acid sequence analyses of both human and murine Class I molecules have demonstrated that the heavy chain is divided into distinct regions: three extracellular domains, a connecting polypeptide, a transmembrane region and a cytoplasmic domain.

The three main extracellular domains, designated α1 (N-terminal), α2 and α3, can be cleaved from cell surfaces with the enzyme papain. These domains each comprise about 90 amino acids. The α2 and α3 domains both have intrachain disulphide bonds and the α3 domain also folds like an Ig constant region. Both human and mouse heavy chains have an N-glycosylated asparagine residue 86 in the α1 domain. Murine heavy chains are also N-glycosylated at residue 176 in α2 and some ($D^b$, $K^d$, $L^d$) have additional carbohydrate side chains at residue 256 in α3. In addition to the major papain cleavage site between α3 and the transmembrane region, there is also a minor cleavage site between the second and third domains.

The transmembrane region consists of about 25 hydrophobic uncharged residues, which probably assume an α-helical conformation and traverse the cell membrane. There is a cluster of about five basic amino acids, arginine and lysine, immediately C-terminal to the transmembrane region. Such highly charged regions are typical of membrane bound proteins and are believed to help to anchor the polypeptide chain in the membrane by interacting with the negatively charged phospholipid headgroups of the inner membrane.

The hydrophilic cytoplasmic domain is about 30 (human) to 40 (mouse) residues long and consists of approximately 50% polar amino acids, particularly serine. Some of these serine residues are phosphorylated. For example, the HLA-A2 heavy chain is phosphorylated by a cyclic AMP-dependent protein kinase at two serine residues in the cytoplasmic domain. Such phosphorylation has been postulated to be involved in transmitting signals from the MHC molecule to appropriate intracytoplasmic mediators.

The Class I light chain, $\beta_2 m$, forms a single Ig-like domain which has strong sequence homology with Ig constant regions. Although it was initially thought that the $\beta_2 m$ associated with the Class I heavy chain primarily through interaction with the α3 domain, in the same way as interdomain Ig interactions, subsequent X-ray crystallographic analysis has revealed a more complex mode of interaction. $\beta_2 m$ is encoded outside the MHC on human chromosome 15 and on mouse chromosome 2. It is a non-polymorphic protein in humans, dimorphic in mice (a single amino acid change at position 85), with a high degree of sequence homology among species implying evolutionary conservation. Association with $\beta_2 m$ is required for expression of Class I antigens at the cell surface and for stabilization of Class I structure.

The three dimensional structure of the extracellular portion obtained by cleavage with papain of several Class I structures has been elucidated. This region contains the α1, α2 and α3 domains and $\beta_2 m$. The α3 and $\beta_2 m$ domains have Ig-folds; that is, they are each composed of two anti-parallel β-pleated sheets, one with four β-strands and one with three β-strands, connected by a disulphide bond. However, the α3 and $\beta_2 m$ domains interact in a manner not found between pairs of constant domains in the known antibody structures.

The α1 and α2 domains have an overall structural similarity. Each consists of an anti-parallel β-pleated sheet spanned by a long α-helical region that is C-terminal to the four β-strands in the sheet. A disulphide bond in a α2 connects a cysteine residue in the N-terminal β-strand to one in the α-helix. The α1 and α2 domains are paired in the HLA molecule such that the four β-strands from each domain form a single antiparallel β-sheet with eight strands. This β-sheet is topped by the helical regions from each domain. The large groove between the α-helices constitutes the binding site for processed protein in the form of peptides. Peptides and their variants capable of binding to this groove will be candidates for evaluation as toxic agents for the treatment of cancer cells according to the invention.

The crystallographic structure of the HLA-A2 molecule has provided a structural basis for the direct binding of peptides to Class I antigen. A binding groove formed by the α1 and α2 domains of the Class I heavy chain was occupied by an ill-defined electron-dense material which was interpreted as peptide(s) filling the binding site. Comparison of the high resolution crystallographic structures of HLA-A2 and HLA-Aw68 has added further insights into the nature of the Class I antigen binding site. The polypeptide backbones of these two Class I antigens are extremely similar, the differences resulting from amino acid side chain differences at 13 positions, six of which are in α1, six in α2 and one in the a 3 domain. The single α3 domain difference (at residue 245) has been shown to contribute to interactions with the CD8 glycoprotein. Ten of the α1 and α2 differences are located at positions lining the floor and side of the peptide-binding groove. The pattern of the amino acid variation between HLA-A2, Aw68 as well as other Class I molecules is similar to the distribution of variable residues obtained from accumulated HLA-A, B and C sequences, which must reflect the conformations with which peptides can occupy the groove. The groove is not a smooth structure but has a number of pockets with which amino acid side chains interact.

Based on this detailed analysis of the three dimensional structures of HLA-A2 and Aw68, a picture has emerged that links the amino acid polymorphism that is such a feature of MHC proteins with limited structural changes within the peptide binding cleft, such as shape, charge distribution and local pockets. These structural changes presumably form the basis for differences in peptide binding affinity which in turn govern responsiveness versus non-responsiveness in the immune response.

In Class I molecules, clusters of conserved residues form hydrogen bonds with the amino and carboxyl termini of bound peptide. These bonds involve conserved residues in the Class I structure, particularly tyrosines at the N-terminus of the peptide and a conserved lysine, as well as other residues at the C-terminus. Peptides of eight to ten residues can apparently be accommodated by maintaining hydrogen bonds at these anchor positions and by bulging out at the center. Peptides can therefore have different conformations at their centers with ends buried in the same pockets.

Techniques for purifying MHC molecules and eluting the bound peptides with acid are known in the art and are described, for example, by Rammensee, H-G., *Die Medizinische Verlagsgesellschaft mbH*:Marburg (1994). In addition, tandem mass spectrometry allows the rapid, convenient and accurate elucidation of smaller peptides, as is known in the art and described, for example, in Hancock, W., ed., *New Methods in Peptide Mapping for the Characterization of Proteins*, CRC Press, Boca Raton, Fla., Publisher (1996).

The many peptide sequences now obtained illustrate that the optimum size for Class I peptides is nine amino acids. While nine amino acid Class I peptides are currently preferred for use according to the invention, shorter or longer sequences may also be useful according to the invention and their usefulness will be determinable by those of ordinary skill employing screening methods such as are described herein. Class II peptides, on the other hand, tend to be longer, at over 15 residues. The anchor residues for Class I peptides, from different allelic products, are clearly identifiable since they lie at fixed points (e.g., position 2 and position 9). By searching protein databases it is possible to determine the origins of the eluted peptides. Peptides from Class I molecules have been estimated to number over 10,000 different sequences. Comparison of different cell types, such as B cells and melanoma, shows that over 90% of the prominent peptides are shared between the two tissues. Many of the peptides eluted from HLA-A2 and HLA-B7 are derived from signal sequences. Those of skill will be able to obtain and evaluate Class I peptide or other peptide sequences for use according to the invention from available sources, including databases such as MHCPEP, maintained by The Walter and Eliza Hall Institute, Parkville, Victoria 3050, Australia. MHCPEP is a curated database comprising peptide sequences known to bind MHC molecules, compiled from published reports as well as from direct submissions of experimental data. The database can be accessed via Internet using Gopher, FTP or WWW by methods known to those of skill.

The present invention also provides for other peptides comprising fragments of the proteins of the invention and polypeptides substantially homologous thereto. The protein peptides of the invention will generally exhibit at least about 80% homology with naturally occurring sequences of the MHC or HLA Class I peptides, typically at least about 85% homology, and more usually at least about 97% homology.

The present invention also includes fusion polypeptides between the MHC or HLA Class I peptides, which may be truncated, and other proteins. For example, homologous polypeptides may be fused with other proteins, or other apoptosis-modulating proteins, resulting in fusion proteins having mixed functionalities. Examples of suitable proteins are members of the Bcl-2 family of proteins, Bak, Bax and the like. Similarly, fusions may be generated with heterologous proteins, for example, the first 16 amino acids of SRC. Such polypeptides may also have amino acid residues which have been chemically modified by phosphorylation, sulfonation, biotinylation, or the addition of other moieties, using methods known in the art. In some embodiments, the modification will be useful labelling reagents, or serve as purification targets, for example, affinity ligands. Fusion polypeptides will typically be made by either recombinant nucleic acid methods or by synthetic polypeptide methods, as are generally described in Sambrook, et al., supra; Merrifield, *J. Amer. Chem. Soc.* 85: 2149–2156 (1963) Merrifield, *Science* 232: 341–347 (1986); and Atherton, et al., *Solid Phase Peptide Synthesis; A Practical Approach,* IRL Press, Oxford (1989).

The peptides, functional equivalents thereof and compositions of the present invention have utility for modulating the growth and differentiation of cells, and preferably of cancer cells, through the apoptotic process. Modulation of the apoptotic process includes deceleration of the rate of apoptosis in a population of cells, or elimination of the cellular apoptotic response to apoptosis inducing agents. Modulation of the apoptotic process also includes induction or acceleration of the apoptosis where it is desirable to increase the rate of cell death or to specifically target a population of cells. For example, the induction of apoptosis in tumor cells or in other cells showing increased proliferation and growth provides an effective therapy to decrease or abolish the growth of these cells, and is a particularly preferred method according to the invention. Of course, while the peptides of the invention exhibit specific toxicity against cancer cells, the actual mechanism of this toxic effect may be a function of a number of pathways; while not intending to be bound by a particular theory, it is believed that modulation of cell cycle events via specific apoptosis induction is responsible for the observed specific toxicity of the peptides, functional equivalents thereof and compositions of the present invention. However, treatment with the peptides of the invention may also involve, for example, necrotic or other events. Those of skill will appreciate that when treating populations of cells, such as cancerous tumor cells, a therapeutic effect may be observed by any number of known clinical endpoints, non-limiting examples of which will include a reduction in the growth rate ol the tumor cell population (which may be recognized as a reduction in the rate at which a palpable tumor or group of tumors increases in size), complete arrest of the growth rate, tumor regression, and the complete elimination or killing of the tumor. The compounds of the present invention also have utility in combatting drug resistance, which is a common problem with current cancer treatments. Drug resistance may be a resistance to apoptosis in general, and thus, the proteins of the present invention may be used to decrease drug resistance. In this embodiment, the compounds of the invention may be used in conjunction with other anti-neoplastic agents. Mechanisms of drug resistance are described, for example, in Remington's Pharmaceutical *Sciences,* 18th Edition, supra. In some embodiments, the compositions of the invention may be used to assay tissue injury and regeneration. A suitable model system for the assay of tissue injury is the thymus of dexamethasone-treated rats, as described in Schwartzman, R., et al., *Endocrinol.* 128(2): 1190–1197 (1991).

The compositions of the present invention thus have utility for a variety of therapeutic indications, including as anti-viral, anti-microbial, or anti-parasitic agents, and particularly as anti-neoplastic agents for the treatment of tumors, including but not limited to tumors of the lung, breast, pancreas and liver, as well as for acute lymphoblastic or myeloid leukemia, chronic myeloid, myelogenous, granulocytic, or lymphatic leukemia, acquired immune deficiency syndrome (AIDS), neurodegenerative diseases, myelodysplasic syndrome, Hodgkin's lymphoma, malignant lymphomas such as non-Hodgkin's lymphoma, or Burkitt's lymphoma, neoplasms and the like. With respect to treatment of cancer, general principles of cancer therapy employing apoptotic agents are known and are set forth, for example, in Green, D. R. et al., Apoptosis and Cancer, in *Principles and Practice of Oncology Updates* Volume 8, J. B. Lippincott Company, January 1994 Number 1, and Gerschenson, L. E., et al. *FASEB J.* 6: 2450–2455 (1992).

The quantities of active ingredient necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients. Animal testing of effective doses for treatment of particular disorders will provide further predictive indication of human dosage. Various considerations are described, for example, Goodman and Gilman's *The Pharmacological Basis of Therapeutics,* 7th Ed., MacMillan Publishing Co, New York (1985), and *Remington's Pharmaceutical Sciences* 18th Ed., Mack Publishing Co., Easton, Penn (1990). Methods for administration are discussed therein, including oral, intravenous, intraperitoneal, intramuscular, transdermal, nasal, iontophoretic administration, and the like.

A key finding of the present inventors is that the toxic effect of the peptides according to the invention is specific. Accordingly, in selecting a dose for use in treating a patient according to the present invention, a treatment regiment will be selected which will achieve a sufficient concentration of the peptide(s) to achieve a toxic effect in the target cells. Because of the specificity of the toxic effect, effective target cell concentrations as low as $10^{-12}$–$10^{-13}$ M are possible. Those of skill will be able to determine an effective dose, which will vary depending upon the manner and mode of administration, in order to achieve such concentrations, although higher and lower concentrations may prove effective for the treatment of cancer cells in vivo. In selecting an appropriate dose, another surprising finding of the present invention will be considered by those of skill; that is, that the toxic effect of the peptides administered according to the present invention is independent of an immune mechanism, and it may be desirable to administer the peptides of the invention at doses and time frames which will avoid an immune response against the peptide being administered. This objective will be achieved, to some extent, by the fact that the small size of many of the peptides useful according to the invention renders them non-immunogenic. Accordingly, it may be desirable to administer the peptides of the present invention at higher doses, in order to achieve a higher effective concentration in the target cancer cell or tissue to achieve the desired toxicity. However, in contrast to immunotherapeutic approaches to the treatment of cancer, the methods of the present invention do not have as their objective the induction of an immune response of CTL against the target cancer cells.

One particularly attractive method for administering the peptides and compositions of the present is inhalation of dry-powder formulations comprising the peptide(s) or peptide composition(s). In order to allow for absorption of the active components through the alveoli into the bloodstream, the powder must be very fine; on the order of 1–5 micron particles. The highly disbursable powder is delivered via an inhaler which generates an aerosol cloud containing the bolus of drug at the top of the inhalation chamber.

The peptides and peptide compositions of the present invention will lend themselves to injection into the bloodstream of a patient suffering from cancer. The half life of the active compositions so administered may be manipulated for best therapeutic effect by employing known drug technologies. One example of such technologies is known as DEPO-FOAM phospholipid spheres (Depo Tech Corp., San Diego, Calif.), which gradually release the active component(s) over a period of days to weeks. This allows for a constant level of systemic concentration with lower initial drug levels and injection frequency.

Known methods of entrapping and stabilizing the peptides of the present invention may be employed to accommodate several different routes of drug delivery. One example of such technologies is the TECHNOSPHERE powder (Pharmaceutical Discovery Corp., Elmsford, N.Y.), which reliably forms two micron diameter spheres under conditions preserving the structural and functional integrity of the active peptide component. The pH-sensitive spheres, when injected into the blood, dissolve and release the active component, which is rapidly absorbed. Fine powders such as these are suitable for pulmonary, oral, intravenous and intraperitoneal administration.

The site of administration and cells will be selected by one of ordinary skill in the art based upon an understanding of the particular degenerative disorder being treated. In addition, the dosage, dosage frequency, and length of course of treatment, can be determined and optimized by one of ordinary skill in the art depending upon the particular degenerative disorder being treated. The particular mode of administration can also be readily selected by one of ordinary skill in the art and can include, for example, oral, intravenous, subcutaneous, intramuscular, etc. Principles of pharmaceutical dosage and drug delivery are known and are described, for example, in Ansel, H. C. and Popovich, N. G., *Pharmaceutical Dosage Forms and Drug Delivery Systems*, 5th Ed, Lea & Febiger, Pub., Philadelphia, Pa. (1990). It is possible, for example, to utilize liposomes to specifically deliver the agents of the invention. Such liposomes can be produced so that they contain additional bioactive compounds and the like such as drugs, radioisotopes, lectins and toxins, which would act at the target site.

Nucleic acid compositions encoding the peptides and peptide variants useful according to the invention will generally be in RNA or DNA forms, mixed polymeric forms, or any synthetic nucleotide structure capable of binding in a base-specific manner to a complementary strand of nucleic acid. Such a nucleic acid embodiment is typically derived from genomic DNA or cDNA, prepared by synthesis, or derived from combinations thereof. The DNA compositions generally include the complete coding region encoding the MHC or HLA Class I peptides, or fragments thereof, e.g., comprising about 4–12 codons, and typically about 9 codons. One or more introns may be present.

The nucleic acids encoding the MHC or HLA Class I peptides or fragments thereof such as C-terminal fragments, may be used to prepare an expression construct for the MHC or HLA Class I peptides. The expression construct normally comprises one or more DNA sequences encoding the MHC or HLA Class I peptides operably linked and under the transcriptional control of a native or other promoter. Usually the promoter will be a eukaryotic promoter for expression in a mammalian cell. The transcriptional regulatory sequences will typically include a heterologous promoter or enhancer which is recognized by the host cell. The selection of an appropriate promoter will depend on the host cell. Convenient expression vectors are commercially available.

By "functional equivalent" is meant a peptide possessing a biological activity or immunological characteristic substantially similar to that of a composition of the invention, and is intended to include "fragments," "variants," "analogs," "homologs," or "chemical derivatives" possessing such activity or characteristic. Functional equivalents of a peptide according to the invention, then, may not share an identical amino acid sequence, and conservative or non-conservative amino acid substitutions of conventional or unconventional amino acids are possible.

Reference herein to "conservative" amino acid substitution is intended to mean the interchangeability of amino acid residues having similar side chains. For example, glycine, alanine, valine, leucine and isoleucine make up a group of amino acids having aliphatic side chains; serine and threonine are amino acids having aliphatic-hydroxyl side chains; asparagine and glutamine are amino acids having amide-containing side chains; phenylalanine, tyrosine and tryptophan are amino acids having aromatic side chains; lysine, arginine and histidine are amino acids having basic side chains; and cysteine and methionine are amino acids having sulfur-containing side chains. Interchanging one amino acid from a given group with another amino acid from that same group would be considered a conservative substitution. Preferred conservative substitution groups include asparagine-glutamine, alanine-valine, lysine-arginine, phenylalanine-tyrosine and valine-leucine-isoleucine.

A "mutant" as used herein refers to a peptide having an amino acid sequence which differs from that of a known peptide or protein by at least one amino acid. Mutants may have the same biological and immunological activity as the known protein. However, the biological or immunological activity of mutants may differ or be lacking. For example, a mutant may lack the biological activity which characterizes a known MHC or HLA Class I peptide, but may be useful as an antigen for raising antibodies against the peptide or for the detection or purification of antibodies thereagainst, or as an agonist (competitive or non-competitive), antagonist, or partial agonist of the toxic function of the peptide.

Modulation of MHC or HLA Class I peptide mediated functions may be effected by agonists or antagonists of MHC or HLA Class I peptides as well. Screening of peptide libraries, compound libraries and other information banks to identify agonists or antagonists of the function of proteins comprising an MHC or HLA Class I peptide is accomplished with assays for detecting the ability of potential agonists or antagonists to inhibit or augment MHC or HLA Class I peptide binding. Suitable labels for use in screening assays according to the invention include a detectable label such as an enzyme, radioactive isotope, fluorescent compound, chemiluminescent compound, or bioluminescent compound. Those of ordinary skill in the art will know of other suitable labels or will be able to ascertain such using routine experimentation. Furthermore, the binding of these labels to the peptides is accomplished using standard techniques known in the art.

The further isolation, purification and sequencing of MHC or HLA Class I peptides from cancer cells for use according to the invention may be accomplished by standard biochemical methods such as, for example, those described in Cantor, C., ed., *Protein purification: Principles and Practice*, Springer Verlag, Heidelberg, Publisher (1982); Hancock, W., ed., *New Methods in Peptide Mapping for the Characterization of Proteins*, CRC Press, Boca Raton, Fla., Publisher (1996).

MHC or HLA Class I peptidomimetic agents are of use in the therapeutic treatment of cancer and viral disease. Peptidomimetics of an MHC or HLA Class I peptide are also provided by the present invention, and can act as drugs for the modulation of cell cycle events in a target cell population by, for example, enhancing the function of proteins, preferably of MHC or HLA Class I peptides. Peptidomimetics are commonly understood in the pharmaceutical industry to include non-peptide drugs having properties analogous to those of those of the mimicked peptide. The principles and practices of peptidomimetic design are known in the art and are described, for example, in Fauchere J., *Adv. Drug Res.* 15: 29 (1986); and Evans, et al., *J. Med. Chem.* 30: 1229 (1987). Peptidomimetics which bear structural similarity to therapeutically useful peptides may be used to produce an equivalent therapeutic or prophylactic effect. Typically, such peptidomimetics have one or more peptide linkages optionally replaced by a linkage which may convert desirable properties such as resistance to chemical breakdown in vivo. Such linkages may include —$CH_2NH$—, —$CH_2S$—, —$CH_2$—$CH_2$—, —$CH$=$CH$—, —$COCH_2$—, —$CH(OH)$ $CH_2$—, and —$CH_2SO$—. Peptidomimetics may exhibit enhanced pharmacological properties (biological half life, absorption rates, etc.), different specificity, increased stability, production economies, lessened antigenicity and the like which makes their use as therapeutics particularly desirable.

It will be appreciated by those of skill that the precise chemical structure of peptides comprising MHC or HLA Class I peptides will vary depending upon a number of factors. For example, a given protein may be obtained as an acidic or basic salt, or in neutral form, since ionizable carboxyl and amino groups are found in the molecule. For the purposes of the invention, then, any form of peptide comprising an MHC or HLA Class I peptide which retains the therapeutic or diagnostic activity of the naturally occurring peptide is intended to be within the scope of the present invention.

The MHC or HLA Class I peptides and other compositions of the present invention may be produced by recombinant DNA techniques known in the art. For example, nucleotide sequences encoding MHC or HLA Class I peptides of the invention may be inserted into a suitable DNA vector, such as a plasmid, and the vector used to transform a suitable host. The recombinant MHC or HLA Class I peptide is produced in the host by expression. The transformed host may be a prokaryotic or eukaryotic cell. Preferred nucleotide sequences for this purpose encoding an MHC or HLA Class I peptide are NUCLEOTIDE SEQ ID NOs: 1–13.

Polynucleotides encoding MHC or HLA Class I peptides may be genomic or cDNA, isolated from clone libraries by conventional methods including hybridization screening methods. Alternatively, synthetic polynucleotide sequences may be constructed by known chemical synthetic methods for the synthesis of oligonucleotides. Such synthetic methods are described, for example, in Blackburn, G. M. and Gait, M. J., Eds., *Nucleic Acids in Chemistry and Biology*, IRL Press, Oxford, England (1990), and it will be evident that commercially available oligonucleotide synthesizers also may be used according to the manufacturer's instructions. One such manufacturer is Applied Bio Systems.

Polymerase chain reaction (PCR) using primers based on the nucleotide sequence data disclosed herein may be used to amplify DNA fragments from mRNA pools, cDNA clone libraries or genomic DNA. PCR nucleotide amplification methods are known in the art and are described, for example, in Erlich, H. A., Ed., *PCR Technology: Principles and Applications for DNA Amplification*, Stockton Press, New York, N.Y. (1989); U.S. Pat. No. 4,683,202; U.S. Pat. No. 4,800,159; and U.S. Pat. No. 4,683,195. Various nucleotide deletions, additions and substitutions may be incorporated into the polynucleotides of the invention as will be recognized by those of skill, who will also recognize that variation in the nucleotide sequence encoding MHC or HLA Class I peptides may occur as a result of, for example, allelic polymorphisms, minor sequencing errors, and the like. The polynucleotides encoding MHC or HLA Class I peptides of the invention may include short oligonucleotides which are useful, for example, as hybridization probes and PCR primers. The polynucleotide sequences of the invention also may comprise a portion of a larger polynucleotide and, through polynucleotide linkage, they may be fused, in frame, with one or more polynucleotide sequences encoding different proteins. In this event, the expressed protein may comprise a fusion protein. Of course, the polynucleotide sequences of the invention may be used in the PCR method to detect the presence of mRNA encoding MHC or HLA Class I peptides in the diagnosis of disease or in forensic analysis.

The sequence of amino acid residues in a protein or peptide comprising an MHC or HLA Class I peptide is designated herein either through the use of their commonly employed three-letter designations or by their single-letter designations. A listing of these three-letter and one-letter designations may be found in textbooks such as Lehninger, A., *Biochemistry*, 2d Ed, Worth Publishers, New York, N.Y.

(1975). When the amino acid sequence is listed horizontally, the amino terminus is intended to be on the left end whereas the carboxy terminus is intended to be at the right end. The residues of amino acids in a peptide may be separated by hyphens. Such hyphens are intended solely to facilitate the presentation of a sequence.

Suitable agents for use according to the invention include MHC or HLA Class I peptides and mimetics, fragments, functional equivalents and/or hybrids or mutants thereof, as well as mutants, and vectors containing cDNA encoding any of the foregoing. Agents can be administered alone or in combination with and/or concurrently with other suitable drugs and/or courses of therapy.

The agents of the present invention are suitable for the treatment of degenerative disorders, including disorders characterized by inappropriate cell proliferation or inappropriate cell death or in some cases, both. Inappropriate cell proliferation will include the statistically significant increase in cell number as compared to the proliferation of that particular cell type in the normal population. Also included are disorders whereby a cell is present and/or persists in an inappropriate location, e.g., the presence of fibroblasts in lung tissue after acute lung injury. For example, such cells include cancer cells which exhibit the properties of invasion and metastasis and are highly anaplastic. Such cells include but are not limited to, cancer cells including, for example, tumor cells. Inappropriate cell death will include a statistically significant decrease in cell number as compared to the presence of that particular cell type in the normal population. Such underrepresentation may be due to a particular degenerative disorder, including, for example, AIDS (HIV), which results in the inappropriate death of T-cells, and autoimmune diseases which are characterized by inappropriate cell death. Autoimmune diseases are disorders caused by an immune response directed against self antigens. Such diseases are characterized by the presence of circulating autoantibodies or cell-mediated immunity against autoantigens in conjunction with inflammatory lesions caused by immunologically competent cells or immune complexes in tissues containing the autoantigens. Such diseases include systemic lupus erythematosus (SLE), rheumatoid arthritis.

Standard reference works setting forth the general principles of immunology include Sell, S., *Immunology. Immunopathology & Immunity*, 5th Ed., Appleton & Lange, Publ., Stamford, CT (1996); Male, D., et al., *Advanced Immunololy*, 3d Ed., Times Mirror Int'l Publishers Ltd., Publ., London (1996); Stites, D. P., and Terr, A. I., *Basic and Clinical Immunology*, 7th Ed., Appleton & Lange, Publ., Norwalk, CT (1991); and Abbas, A. K., et al., *Cellular and Molecular Immunology*, W. B. Saunders Co., Publ., Philadelphia, Pa. (1991).

The MHC or HLA Class I peptides, mimetics, agents and the like disclosed herein, as well as vectors comprising nucleotide sequences encoding them or their corresponding antisense sequences, and hosts comprising such vectors, may be used in the manufacture of medicaments for the treatment of diseases including cancer.

The invention may be appreciated in certain aspects with reference to the following examples, offered by way of illustration, not by way of limitation.

EXAMPLES

METHODS AND MATERIALS

In vivo Apoptosis Assay.

The test for apoptosis in vivo was based on the use of the diffusion chamber described in detail by Resnicoff, M., et al., *Cancer Res*. 55: 2463–2469 (1995). According to this method, the cells are placed in a diffusion chamber that allows the passage of nutrients, antigens, antibodies, etc., but not of intact cells. The sterilized chamber is loaded with cells and then inserted into the subcutaneous tissue of rats or mice; after 24 hours, (or at other times, depending on the experiment) the chamber is removed and the number of cells in the chamber is determined with a hemocytometer, and expressed as a percentage of the original inoculum. The cells are also stained with trypan blue for viability; in the experience of the inventors, surviving cells are >95% viable.

For in vivo effects, $5 \times 10^5$ cells (C6 and CaOV-3 were both used for these studies) were placed in diffusion chambers and implanted into the s.c. tissue of the animals. Once the skin was sutured, the peptides were injected s.c. next to the chambers at the indicated concentrations in a final volume of 0.2 ml. Twenty-four hours later, the chambers were removed from the animals and the cells were quantitatively recovered.

Synthesis of Peptides.

All chemicals were of analytical grade and were used without further purifications. Various solvents were purchased from Fisher Scientific Co. and Aldrich Co. Na-Fmoc amino acids and other chemical reagents were purchased from Fisher Scientific Co, Novabiochem, Fluka and Perseptive Biosystems. Fmoc-tris(alkoxy)benzylamide linked polystyrene resin (PAL-support) with a substitution level of 0.38 mmol/g and polyethylene glycol graft polystyrene resin (PAL-PEG-support) with substitution level of 0.16 mmol/g were both purchased from Perseptive Biosystems.

Peptides were prepared by solid phase synthesis with Fmoc-strategy using an Applied Biosystems model 430A peptide and Perseptive Biosystems 9050 Pepsynthesizer Plus. The side chain-protecting groups of N(-Fmoc) amino acids were: Boc for Lys, OtBu for Asp and Glu, Pmc for Arg, tBu for Ser and Thr, and Trt for Asn, Gln, His and Cys. The four-fold excess of N(-Fmoc) amino acid, HBTU and HOBt, and ten-fold excess of DIPEA, were used in every coupling reaction step. Removal of the N-terminal Fmoc group was accomplished by 20% piperidine in DMF. The coupling and deprotection steps were repeated for all the amino acid residues. The cleavage of a peptide from the resin was carried out with reagent K (TFA:Phenol:thioanisole:ethandithiol:H2O/10:0.75:0.5:0.25:0.5) for 2 hours at room temperature with gentle stirring. The mixture was then filtered directly into ice-cold methyl t-butyl ether. The resulting suspension was transferred into a centrifuge tube and centrifuged for 10 minutes at 2000×g at room temperature. The supernatant was discarded and the precipitate was resuspended in methyl t-butyl ether, and again centrifuged for 10 minutes. The procedure was repeated twice before the precipitate was dissolved in aqueous solvent and lyophilized. The crude peptide was then purified by preparative RP-HPLC using Dynamax-300 Å C18 25 cm×21.4 mm I.D. column with flow rate of 9 ml/min. The fractions containing the peptide were pooled together and lyophilized.

The purity of the final products was assessed by analytical RP-HPLC, capillary electrophoresis and MALD-TOF MS. A gradient analytical RP-HPLC system, comprising a Waters 600E multisolvent delivery system, Waters 490E programmable multiwavelength detector setting at 206 nm and 280 nm, Waters 715 Ultra wisp autosampler and Maxima 820 chromatography workstation for data acquisition, was used. For a preparative RP-HPLC, a system comprising two Applied Biosystems 400 solvent delivery systems, Applied Biosystems 783A programmable absorbance detector and pump controller, Pharmacia, LKB REC120 chart recorder and Waters fraction collector was used. In both HPLC systems, solvent A was 99.9% water and 0.1% TFA, and solvent B was 99.9% acetonitrile and 0.1% TFA. Capillary electrophoresis was performed by using Applied Biosystems 270A-HT systems equipped with 72 cm×0.05 mm I.D. fused silica capillary at 30° C. Injection was hydrodynamic for 3 seconds at 5" Hg and the applied voltage during the run was 20 kV. Matrix assisted laser desorption time of flight mass spectra (MALD-TOF MS) were taken using Biomolecular Separations LDI1700 with sinapinic acid and α-cyano-4-hydroxycinnamic acid solutions as matrices.

RESULTS

Cytotoxicity of MHC-Associated Peptides.

To demonstrate the use of MHC or HLA Class I peptides for induction of apoptosis in cancer cells, three peptides were tested for their cytotoxicity in the diffusion chamber assay: 1) LLDGTATLRL [SEQ ID NO.1] (from gp100), involved in regression of human melanoma (Kawakami et al. 1994); 2) YLEPGPVTA [SEQ ID NO.2], recognized by melanoma-specific human CTL lines (Cox et al, 1994); and 3) FECNTAQPG [SEQ ID NO.3], derived from connexin 37, that induces CTL responses against murine lung carcinoma (Mandelboim, et al., 1994). For each of these peptides, a control peptide having the same amino acid composition, but in scrambled order (controls), was also tested. C6 cells were preincubated with the peptides at a concentration of $10^{-5}$M and transferred to the diffusion chamber (see Methods and Materials). Cell number was determined after 24 hours in the diffusion chamber transplanted into the subcutaneous tissue of rats. With the 3 test peptides, recovery ranged from 5–7.5% of the inoculated cells, indicating that these peptides exhibited potent cytotoxicity under those conditions. Recovery with the control peptides was >200%, indicating that cells were not killed but proliferated. These results suggest that the cytotoxic activity of the test peptides was specific.

Effect of Mutations on the Ability of MHC-associated Peptides to Induce Apoptosis in vivo.

Two of the three peptides were selected for further studies of the effects of mutations on the ability to induce apoptosis. Several point mutations were introduced into the peptide YLEPGPVTA [SEQ ID NO.2]. These mutant peptides were tested on C6 cells in the diffusion chamber assay following preincubation at a concentration of $10^{-5}$ M. The results (Table 1) indicate that some mutations do not affect the ability of these peptides to induce apoptosis, while others completely abrogate this capacity. Mutations at tyrosine in position 1, or the two prolines in positions 4 and 6, effectively inactivated peptide no. 2. An exception to this observation was seen when the prolines were replaced by an N-methyl amino acid. Mutations at E3 or T8 had little effect, but when both residues were mutated, recovery increased to 77%. D-amino acid versions of the LLDGTATLRL [SEQ ID NO.1] and YLEPGPVTA [SEQ ID NO.2] peptides, in which the amino acid sequence is reversed (i.e., LRLTATGDLL [SEQ ID NO.16] and ATVPGPELY, [SEQ ID NO.15] respectively) were as effective as the L-amino acid sequences.

Dose-response for Peptide-induced Apoptosis.

In order to determine the minimum concentration of these peptides that still would induce apoptosis in vivo, C6 cells were preincubated with different concentrations of the YLRPGPVTA and D-amino acid LRLTATGDLL [SEQ ID NO.16] peptides and recovery of viable cells was determined after 24 hours in the diffusion chamber. Table 4 shows the results. Recovery of inoculated cells was only 18% when pretreated with peptide YLRPGPVTA [SEQ ID NO.4] at a concentration of $10^{-12}$ M. Pretreatment with the D-amino acid sequence LRLTATGDLL [SEQ ID NO.16] resulted in similar recovery of C6 cells at a concentration of $10^{-13}$M. These concentrations are 7–8 orders of magnitude lower than the concentration at which the inactive peptides were tested.

Evidence for Induction of Apoptosis by Active Peptides.

In order to determine that the loss of cells upon treatment with active peptides was due to the induction of apoptosis, the presence of apoptotic cells within the diffusion chamber was determined at several time intervals by FACS analysis (Sell, et al. (1995)). FIG. 1 represents a typical experiment using C6 cells. C6 cells in FIG. 1(A) were treated with an active peptide (YLEPGPVTA) [SEQ ID NO.2]; FIG. 1(B) shows results for C6 cells treated with a control peptide (SMAPGNYSV) [SEQ ID NO.14]. In both cases, the cells had been incubated in vivo for 90 minutes in a diffusion chamber as described herein. Apoptotic cells are detectable in FIG. 1(A), but not in FIG. 1(B). Similar results were obtained at several time intervals thereafter.

In addition, one of the common pathways of apoptotic injury is through the ICE proteins (Henkart (1996)). The activation of ICE and ICE-like proteins is inhibited by the p35 protein of baculovirus (Clem and Miller (1994)), which can also be functional in mammalian cells (Rabizadeh, et al. (1993). To determine whether the synthetic peptides caused apoptosis through the ICE pathway, a plasmid expressing the p35 protein was stably introduced into C6 cells. C6 and C6/p35 cells were then tested for apoptosis in the diffusion chambers, using the synthetic peptide YLRPGPVTA [SEQ ID NO.4]. FIG. 2 is a composite picture showing the expression of p35 in the various cell lines, and, below each lane, the percentage of cells recovered from the diffusion chamber. Only C6 cells and C6 cells stably transfected with the empty vector underwent apoptosis when treated with the peptide; the two clones expressing the p35 protein grew in the diffusion chamber equally well whether untreated or incubated with the synthetic peptide.

Selected Pepfides Induce Apoptosis when Injected in vivo.

The purpose of this experiment was to show that the synthetic peptides induced apoptosis when injected in vivo, and that their effect extended to human tumor cells. Human ovarian carcinoma cells CaOV3 (Resnicoff, et al. (1993)) were loaded into a diffusion chamber, and the chamber was inserted into the subcutaneous tissue of mice. The animals were then injected, also subcutaneously next to the chamber, with 0.2 ml of a 0.05 mM solution of four different peptides, and the number of cells was determined 24 hours later. The results (Table 2) clearly show that active peptides can induce apoptosis of tumor cells, even when injected into mice. The control peptide had no effect, and the number of cells more than doubled. CaOV3 cells also undergo apoptosis, as determined by FACS analysis.

Selected Peptides Inhibit Tumorigenesis in Syngeneic Rats.

C6 cells pre-incubated with various concentrations ($10^{-12}$, $10^{-10}$, $10^{-8}$, and $10^{-55}$ M) of the peptide YLRPGPVTA [SEQ ID NO.2] were injected simultaneously into nude mice and the time of appearance of subcutaneous tumors was determined. In parallel experiments, the percentage of cells killed in the diffusion chamber assay was determined. From the percentage of cells killed, the expected delay in the appearance of tumors in mice was calculated as described previously (Resnicoff, et al., Cancer Res. 55:3739 (1995)). The results are summarized in Table 3. There is a concentration-dependent inhibition of tumorigenesis in C6 cells pre-treated with the active peptide. An inactive peptide had no effect. The time of appearance of tumors is slightly more delayed than expected from the percentage of cells killed in 24 hours in the diffusion chamber assay, a phenomenon previously observed also with antisense oligodeoxynucleotides to the IGF-IR RNA (Resnicoff, et al., *Cancer Res.* 55:3739 (1995)).

A similar inhibition of tumorigenesis was observed using the D-amino acid peptide LRLTATGDLL [SEQ ID NO. 16]. In this case, the peptide (all D-aa, sequence from Kawakami, et al. (1994)) was injected s.c. into nude mice (0.1 ml, at the indicated concentrations), simultaneously with C6 cells (105 cells in 0. ml) and next to them. The animals were followed for tumor development. The results were as follows: For C6 cells without peptide injection, the tumors appeared after 4 days; for a peptide injection at $10^{-10}$ to $10^{-12}$ M, tumors appeared after 11 days.

The induction of apoptosis by MHC-associated peptides is a specific phenomenon that cannot be explained by an aspecific toxicity of the synthetic peptides. Active synthetic peptides are capable of inducing apoptosis at concentrations of $10^{-12}$–$10^{-13}$ M, while control peptides are inactive even at concentrations as great as $10^{-5}$ M. In addition, selected point mutations in the active synthetic peptides completely inactivate them. The direct induction of apoptosis by these peptides was a surprising finding.

Two different approaches were used to demonstrate apoptosis. In some experiments, the cells were pre-incubated with the peptides, then loaded in a diffusion chamber (Resnicoff, M., et al., *Cancer Res.* 55: 2463–2469 (1995)), which was then implanted into the subcutaneous tissue of rats or mice. The apoptotic effect of MHC-associated peptides is independent of an immune mechanism. This statement is based on the following considerations: 1) in the experiments of Tables 1 and 2, the peptides induce apoptosis in vivo in the short period of 24 hours, (onset of apoptosis was seen in a period as short as 90 minutes, see FIG. 1) which seems to exclude an immune response, since the animals were naive; 2) the cells were in a diffusion chamber, which is impermeable to cells; and 3) although the synthetic peptides are of human origin, they were equally active on rat and on human tumor cells. In fact, experiments indicate that these peptides induce apoptosis in vivo on a variety of tumor cell lines, regardless of the type of tumor or species, a surprising and unexpected finding. In summary, the present experiments conclusively demonstrate that MHC-associated peptides can induce apoptosis of tumor cells in vivo by a non-immune mechanism.

TABLE 1

Effect of Point Mutations on Induction of Apoptosis In Vivo in C6 Cells by MHC Class I Peptides

| Peptide | % Recovery (24 hs) | Protection from wild type cell challenge |
|---|---|---|
| YLEPGPVTA [SEQ ID NO. 2] | 3.0 | yes |
| YLRPGPVTA [SEQ ID NO. 4] | 3.5 | yes |
| YLEXGXVTA (X: N-Methyl-A) [SEQ ID NO. 5] | 6.5 | yes |
| YLAPGPVTA [SEQ ID NO. 7] | 7.4 | yes |
| YLEPGPVAA [SEQ ID NO. 8] | 9.3 | yes |
| YLEPGPATA [SEQ ID NO. 9] | 11.0 | yes |
| YLEPGPVKA [SEQ ID NO. 6] | 12.0 | yes |
| YLEPAPVTA [SEQ ID NO. 10] | 70.0 | no |
| YLRPGPVRA [SEQ ID NO. 11] | 77.0 | no |
| YAEPGPVTA [SEQ ID NO. 17] | 186.0 | no |
| YLEAGPVTA [SEQ ID NO. 18] | 224.0 | no |
| ALEPGPVTA [SEQ ID NO. 19] | 224.0 | no |

TABLE 1-continued

Effect of Point Mutations on Induction of Apoptosis In Vivo in C6 Cells by MHC Class I Peptides

| Peptide | % Recovery (24 hs) | Protection from wild type cell challenge |
|---|---|---|
| YLEPGAVTA [SEQ ID NO. 20] | 260.0 | no |
| LLDGTATLRL [SEQ ID NO. 1] | 5.0 | yes |
| ATVPGPELY (D-amino acid) [SEQ ID NO. 15] | 6.0 | yes |
| LRLTATGDLL (D-amino acid) [SEQ ID NO. 16] | 4.9 | yes |

Synthetic peptide sequences listed above were tested at $5 \times 10^{-5}$ M on C6 cells. Tests for apoptosis and for protection from subsequent challenge with C6 cells are described herein. Point mutations are shown in bold characters.

TABLE 2

Selected Peptides Induce Apoptosis In Vivo in Human Ovarian Carcinoma Cells.

| Peptide | Percent Recovery |
|---|---|
| YLRPGPVTA [SEQ ID NO. 4] | 3.0 |
| YLEPGPVTA [SEQ ID NO. 2] | 0.2 |
| LRLTATGDLL [SEQ ID NO. 16] | 6.6 |
| YLEPGAVTA (control) [SEQ ID NO. 20] | 280 |

CaOV3 cells (human ovarian carcinoma cells, $5 \times 10^5$ cells) were placed without any previous treatment into diffusion chambers that were then implanted into the subcutaneous tissue of Balb/c mice. Animals were then injected subcutaneously next to the chambers either with 0.2 ml of a 0.05 mM solution of one of the three test peptides or with 0.2 ml of a 0.05 mM solution of the control peptide. The results summarized demonstrate that the three test peptides induce apoptosis in vivo of human tumor cells.

TABLE 3

Tumorigenesis in nude mice.

| Concentration of Peptide YLRPGPVTA [SEQ ID NO. 4] | % Recovery | Expected Delay (days) | Palpable Tumors (days) |
|---|---|---|---|
| None | >200 | 4 | 4 |
| $10^{-12}$M | 18 | 8 | 11 |
| $10^{-10}$M | 4.5 | 10 | 14 |
| $10^{-8}$M | 2.1 | 11 | 15 |
| $10^{-5}$M | 0.3 | 14 | 21 |

C6 cells were incubated with the synthetic peptide at the indicated final concentrations for 24 hours in serum-free medium before injection into the subcutaneous tissue of seven week-old male Balb/c nude mice. Percentage recovery was determined using the diffusion chamber assay as described herein. Expected Delay is the number of days after injection before the tumors should become palpable, based on survival in vivo estimated by percentage of cells recovered. The last column shows the actual number of days after injection when tumors became palpable. Three nude mice were used in each experimental condition.

Dose Response of Peptide-induced Apoptosis.

The concentration of peptides required to induce apoptosis of C6 tumor cells in the diffusion chamber was tested with two of the peptides, and the results are given in Table 4.

TABLE 4

| Peptide | Concentration | Percent Recovery |
| --- | --- | --- |
| YLRPGPVTA | $10^{-5}$M | 0.3 |
| [SEQ ID NO. 4] | $10^{-8}$M | 2.1 |
|  | $10^{-10}$M | 4.5 |
|  | $10^{-12}$M | 18.0 |
| LRLTATGDLL (D-aa) | $10^{-5}$M | 0.5 |
| [SEQ ID NO. 16] | $10^{-8}$M | 3.0 |
|  | $10^{-12}$M | 6.6 |
|  | $10^{-13}$M | 18.0 |

Table 4 shows that these two peptides are essentially equal in their ability to induce apoptosis of tumor cells.

Viral MHC Class I Peptides Induce Apoptosis In Vivo

Experiments were carried out using synthetic MHC Class I Peptides other than tumor antigens to illustrate the broad scope of the present invention and the effective use of screening methods as described to identify useful peptides for the induction of apoptosis in cancer cells.

In the first of these experiments, MHC Class I peptides derived from Human Papilloma Virus Type 16 (HPV-16) E7 protein were selected for screening with C6 glioblastoma cells using the diffusion chamber method described herein. These viral peptides were designated HPV-16 E7$_{86-93}$ (amino acid sequence: TLGIVCPI [SEQ ID NO.21]) and HPV-16 E7$_{11-20}$ (amino acid sequence: YMLDLQPETT [SEQ ID NO.22]). Ressing, et al., *Cancer Res.* 56:582–588 (1996). C6 rat glioblastoma cells were pre-treated with these peptides at a final concentration of 50 μM for 24 hours in serum-free medium. Control cells were pre-treated without peptide. The assay was carried out using the diffusion chamber implanted in the subcutaneous tissue of rats for 24 hours, as described.

The results are shown in Table 5.

TABLE 5

| Condition | Recovery (%) |
| --- | --- |
| C6 with no peptide treatment | 204 |
| C6 + HPV-16 E7 $_{86-93}$ | 27 |
| C6 + HPV-16 E7 $_{11-20}$ | 13 |

In a second experiment, a synthetic peptide corresponding to one derived from influenza virus, designated M1$_{58-66}$·66 (amino acid sequence: GLGFVPTL [SEQ ID NO.23]), was used to pre-treat C6 glioblastoma cells for 24 hours at a final concentration of $10^{-4}$M in serum-free medium. Controls were treated with medium, but without the M1$_{58-66}$ peptide. Following implantation of the cells in mice, using the diffusion chamber method described herein, and in vivo growth for 25 hours, the chambers were removed and the cells were quantitatively recovered. The results are shown in Table 7.

TABLE 6

| Condition | Recovery (%) |
| --- | --- |
| C6 with no peptide treatment | 260 |
| C6 + M1$_{58-66}$ | 23.4 |

The results of these two experiments demonstrate that peptides not identified as tumor antigens induce apoptosis in vivo in cancer cells, and illustrate that the screening methods disclosed herein, or, indeed, other in vivo and in vitro cell death detection methods known in the art (including, but not limited to, TdT-mediated dUTP Nick End Labeling (TUNEL) and In Situ Nick Translation (ISNT) (Pihlgren, M., et al., *Biochemica* 3[1996]: 12–14 (1996))) may be employed by those of skill, having the benefit of knowledge of the present invention, to identify MHC Class I peptides and other peptides useful according to the invention for the treatment of cancer.

TABLE 7

| TISSUE OF ORIGIN | CELL LINE | CELL TYPE | SOURCE |
| --- | --- | --- | --- |
| Neuronal Tissue | IMR-32 | Neuroblastoma | ATCC #CCL 127 |
|  | SK-N-SH | Neuroblastoma | ATCC #HTB 11 |
| Bladder | SCaBER | Squamous cell | ATCC #HTB 3 |
| Bladder | T24 | Transitional cell | ATTC #HTB 4 |
| Bone | RD-ES | Ewing's Sarcoma | ATCC #HTB 166 |
| Brain | U-373 MG | Glioblastoma | ATCC #HTB 17 |
|  | U-87 MG | Glioblastoma | ATCC #HTB 14 |
| Breast | BT-549 | Ductal Carcinoma | ATCC #HTB 122 |
|  | MCF7 | Adenocarcinoma | ATCC #HTB 22 |
|  | MDA-MB-468 | Adenocarcinoma | ATCC #HTB 132 |
| Colon | COLO 201 | Adenocarcinoma | ATCC #CCL 224 |
|  | LoVo | Adenocarcinoma | ATCC #CCL 229 |
|  | LS 174T | Adenocarcinoma | ATCC #CL 188 |
|  | HT-29 | Adenocarcinoma | ATCC #HTB 38 |
| Cervix | HeLa | Epitheloid Carcinoma | ATCC #CCL 2 |
| Kidney | A-704 | Adenocarcinoma | ATCC #HTB 45 |
|  | CAKI-1 | Clear cell Carcinoma | ATCC #HTB 46 |
| Lung | LU-99 | Large cell Carcinoma | SynPhar Laboratories Alberta, Canada |
|  | SW-1573 | Small Cell Carcinoma | Dr. Robert Arcea DFCI, Boston, MA |
|  | SW2 | Small Cell Carcinoma | Dr. Sam Bernal DFCI, Boston MA |
| Lymph Node | Namalwa | B Cell Lymphoma | ATCC #CRL 1432 |
| Mouth | KB (2D1) | Epidermoid Carcinoma | ATCC #CCL 17 |
| Ovary | OVCAR-3 | Adenocarcinoma | ATCC #HTB 161 |
|  | SK-OV-3 | Adenocarcinoma | ATCC #HTB 77 |
| Pancreas | PANC-1 | Epitheloid Carcinoma | ATCC #CRL 1469 |
| Peripheral Blood | HL-60 | Promyelocytic leukemia | ATCC #CCL 240 |
|  | MOLT-4 | T Cell leukemia | ATCC #CRL 1582 |
| Prostate | DU 145 | Carcinoma | ATCC #HTB 81 |
|  | PC-3 | Adenocarcinoma | ATCC #CRL 1435 |
|  | LNCaP FEC | Adenocarcinoma | ATCC #CRL 1740 |
| Skin | SK-MEL-37 | Melanoma | Dr. Aaron Lerner Yale Medical School |
|  | Hs 695T | Melanoma | ATCC #HTB 137 |
|  | A-375 | Melanoma | ATCC #CRL 1619 |
|  | SqCc/Y1 | Squamous cell | Dr. Alan Sartorelli Yale Medical School |
| Stomach | AGS | Adenocarcinoma | ATCC #CRL 1739 |

All publications mentioned in this specification are herein incorporated by reference, to the same extent as if each individual publication was specifically and individually indicated to be incorporated by reference. It will be understood that the invention is capable of further modifications and this application is intended to cover any variations, uses, or adoptions of the invention including such departures from the present disclosure as come within known or customary practice within the art to which the invention pertains, and is intended to be limited only by the appended claims.

What is claimed is:

1. A method of killing a cancer cell in a patient, comprising administering to said patient an amount of an MHC or HLA Class I peptide sufficient to kill said cancer cell independent of an immune mechanism.

2. The method of claim 1, wherein said peptide is selected by use of an in vivo or in vitro apoptosis screening assay.

3. The method of claim 2, wherein said assay is an in vivo diffusion chamber assay.

4. The method of claim 2, wherein the cells used for said assay are cancer cells obtained from said patient.

5. The method of claims 1, 2, 3, or 4, wherein said MHC or HLA Class I peptide is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13.

6. A composition comprising an MHC or HLA Class I peptide selected from the group consisting of SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12 and SEQ ID NO: 13, and a pharmaceutically acceptable carrier.

7. A method for the induction of apoptosis in a cancer cell in vivo comprising administering to a patient a composition of claim 6.

8. A method of arresting the growth of a cancerous tumor in a patient, comprising administering to said patient an amount of an MHC or HLA Class I peptide sufficient to arrest the growth of said tumor independent of an immune mechanism.

9. The method of claim 8, wherein said tumor exhibits regression.

10. The method of claim 8, wherein said tumor is killed.

11. The method of claim 1, wherein the MHC or HLA Class I peptide is a D-amino acid peptide.

12. The method of claim 8, wherein the MHC or HLA Class I peptide is a D-amino acid peptide.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:1:

Leu Leu Asp Gly Thr Ala Thr Leu Arg Leu
1               5                   10

(2) INFORMATION FOR SEQ ID NO:2:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:2:

Tyr Leu Glu Pro Gly Pro Val Thr Ala
1               5

(2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:3:

Phe Glu Cys Asn Thr Ala Gln Pro Gly
1               5

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:4:

Tyr Leu Arg Pro Gly Pro Val Thr Ala
1               5

(2) INFORMATION FOR SEQ ID NO:5:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:5:

Tyr Leu Glu Xaa Gly Xaa Val Thr Ala
1               5

(2) INFORMATION FOR SEQ ID NO:6:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:6:

Tyr Leu Glu Pro Gly Pro Val Lys Ala
1               5

(2) INFORMATION FOR SEQ ID NO:7:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:7:

Tyr Leu Ala Pro Gly Pro Val Thr Ala
1               5

(2) INFORMATION FOR SEQ ID NO:8:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:8:

Tyr Leu Glu Pro Gly Pro Val Ala Ala
1               5

(2) INFORMATION FOR SEQ ID NO:9:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:9:

Tyr Leu Glu Pro Gly Pro Ala Thr Ala
1               5

(2) INFORMATION FOR SEQ ID NO:10:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:10:

Tyr Leu Glu Pro Ala Pro Val Thr Ala
1               5

(2) INFORMATION FOR SEQ ID NO:11:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:11:

Tyr Leu Arg Pro Gly Pro Val Arg Ala
1               5

(2) INFORMATION FOR SEQ ID NO:12:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:12:

Ala Thr Val Pro Gly Pro Glu Leu Tyr
1               5

(2) INFORMATION FOR SEQ ID NO:13:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:13:

Leu Arg Leu Thr Ala Thr Gly Asp Leu Leu
1               5                   10

(2) INFORMATION FOR SEQ ID NO:14:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:14:

Ser Met Ala Pro Gly Asn Tyr Ser Val
1               5

(2) INFORMATION FOR SEQ ID NO:15:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:15:

Ala Thr Val Pro Gly Pro Glu Leu Tyr
1               5

(2) INFORMATION FOR SEQ ID NO:16:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:16:

Leu Arg Leu Thr Ala Thr Gly Asp Leu Leu
1               5                   10

(2) INFORMATION FOR SEQ ID NO:17:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:17:

Tyr Ala Glu Pro Gly Pro Val Thr Ala
1               5

(2) INFORMATION FOR SEQ ID NO:18:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:18:

Tyr Leu Glu Ala Gly Pro Val Thr Ala
1               5

(2) INFORMATION FOR SEQ ID NO:19:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:19:

Ala Leu Glu Pro Gly Pro Val Thr Ala
1               5

(2) INFORMATION FOR SEQ ID NO:20:

(i) SEQUENCE CHARACTERISTICS:
            (A) LENGTH: 9 amino acids
            (B) TYPE: amino acid
            (C) STRANDEDNESS: single
            (D) TOPOLOGY: linear -continued

```
    (ii) MOLECULE TYPE: peptide (iii) HYPOTHETICAL: NO (iv) ANTI-SENSE: NO (xi) SEQUENCE DESCRIPTION: SEQ ID NO:20:

Tyr Leu Glu Pro Gly Ala Val Thr Ala
1               5

(2) INFORMATION FOR SEQ ID NO:21:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:21:

Thr Leu Gly Ile Val Cys Pro Ile
1               5

(2) INFORMATION FOR SEQ ID NO:22:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:22:

Tyr Met Leu Asp Leu Gln Pro Glu Thr Thr
1               5                   10

(2) INFORMATION FOR SEQ ID NO:23:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:23:

Gly Ile Leu Gly Phe Val Pro Thr Leu
1               5
```